US 6,403,535 B1

(12) United States Patent
Müller et al.

(10) Patent No.: US 6,403,535 B1
(45) Date of Patent: Jun. 11, 2002

(54) SUBSTITUTED THIAZOL(IN) YLIDENEAMINO SULFONYLAMINO (THIO) CARBONYL-TRIAZOLINONES

(75) Inventors: Klaus-Helmut Müller, Düsseldorf; Klaus König, Odenthal; Johannes Rudolf Jansen, Monheim; Ernst Rudolf F. Gesing, Erkrath; Mark Wilhelm Drewes, Langenfeld, all of (DE); Markus Dollinger, Overland Park, KS (US); Ingo Wetcholowsky, Cond. Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,479

(22) PCT Filed: Sep. 13, 1999

(86) PCT No.: PCT/EP99/06753
§ 371 (c)(1),
(2), (4) Date: Apr. 27, 2001

(87) PCT Pub. No.: WO00/17196
PCT Pub. Date: Mar. 30, 2000

(30) Foreign Application Priority Data

Sep. 24, 1998 (DE) .......................... 198 43 766

(51) Int. Cl.⁷ .................... A01N 47/38; C07D 417/12
(52) U.S. Cl. ...................... 504/268; 548/194
(58) Field of Search ............... 348/194; 504/268

(56) References Cited

U.S. PATENT DOCUMENTS

| 5,085,684 A | 2/1992 | Müller et al. ................. 71/92 |
| 5,534,486 A | 7/1996 | Müller et al. ................ 504/273 |
| 5,541,337 A | 7/1996 | Müller et al. ................ 548/263.6 |
| 5,552,369 A | 9/1996 | Findeisen et al. ............. 504/273 |
| 5,597,939 A | 1/1997 | Müller et al. ................. 558/8 |
| 5,652,372 A | 7/1997 | Müller et al. ................ 548/263.4 |
| 5,861,358 A | 1/1999 | Findeisen et al. ............. 504/273 |
| 5,869,681 A | 2/1999 | Müller et al. ................ 548/263.6 |
| 5,972,844 A | 10/1999 | Müller et al. ................ 504/273 |

FOREIGN PATENT DOCUMENTS

| DE | 3936623 | 5/1991 |
| DE | 4411913 | 10/1995 |
| EP | 0341489 | 11/1989 |
| EP | 0422469 | 4/1991 |
| EP | 0425948 | 5/1991 |
| WO | 93/24482 | 12/1993 |

Primary Examiner—Robert Gerstl
(74) Attorney, Agent, or Firm—Joseph C. Gil

(57) ABSTRACT

The invention relates to novel substituted thiazol(in) ylidenaminosulphonyl-amino(thio)carbonyl-triazolinones of the formula (I)

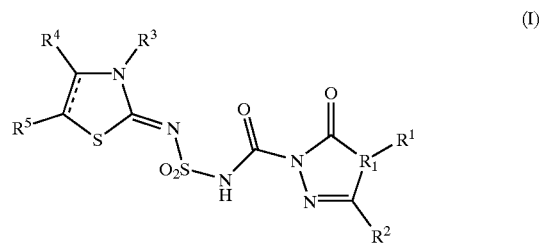

in which

Q represents oxygen or sulphur, $R^1$ represents hydrogen, amino, alkylideneamino or represents an in each case optionally substituted radical from the group consisting of alkyl, alkoxy, alkylamino, dialkylamino, alkanoylamino, alkenyl, alkinyl, alkenyloxy, cycloalkyl, cycloalkylalkyl, cycloalkylamino, aryl and arylalkyl, $R^2$ represents hydrogen, cyano, halogen or represents an in each case optionally substituted radical from the group consisting of alkyl, alkoxy, alkylthio, alkylsulphinyl, alkylsulphonyl, alkylamino, dialkylamino, alkenyl, alkinyl, alkenyloxy, alkenylthio, alkenylamino, cycloalkyl, cycloalkylalkyl, cycloalkyloxy, cycloalkylthio, cycloalkylamino, aryl, aryloxy, arylthio, arylamino, arylalkyl, arylalkoxy, arylalkylthio and arylalkylamino, $R^3$ represents an in each case optionally substituted radical from the group consisting of alkyl, alkoxy, alkenyl, alkinyl, cycloalkyl, cycloalkylalkyl, aryl and arylalkyl, $R^4$ represents hydrogen, cyano, halogen or optionally substituted alkyl, $R^5$ represents hydrogen, cyano, halogen or optionally substituted alkyl, and to salts of compounds of the formula (I), to processes for preparing the novel compounds and to their use as herbicides.

7 Claims, No Drawings

SUBSTITUTED THIAZOL(IN) YLIDENEAMINO SULFONYLAMINO (THIO) CARBONYL-TRIAZOLINONES

The invention relates to novel substituted thiazol(in)ylideneaminosulphonylamino-(thio)carbonyl-triazolinones, to a plurality of processes for their preparation and to their use as herbicides.

It is already known that certain substituted thiazol(in)ylideneaminosulphonyl-amino(thio)carbonyl-triazolinones have herbicidal properties (cf. EP 341 489, EP 422 469, EP 425 948, EP 431 291, EP 507 171, WO 93/24482, WO 94/08979, WO 95/27703, WO 96/22982). However, the activity of these compounds is not entirely satisfactory.

This invention, accordingly provides novel substituted thiazoli(di)nylimino-sulphonylamino(thio)carbonyl-triazolinones of the general formula (I),

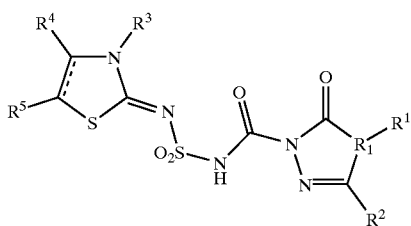

(I)

in which

Q represents oxygen or sulphur, $R^1$ represents hydrogen, amino, alkylideneamino or represents an in each case optionally substituted radical from the group consisting of alkyl, alkoxy, alkylamino, dialkylamino, alkanoylamino, alkenyl, alkinyl, alkenyloxy, cycloalkyl, cycloalkylalkyl, cycloalkylamino, aryl and arylalkyl, $R^2$ represents hydrogen, cyano, halogen or represents an in each case optionally substituted radical from the group consisting of alkyl, alkoxy, alkylthio, alkylsulphinyl, alkylsulphonyl, alkylamino, dialkylamino, alkenyl, alkinyl, alkenyloxy, alkenylthio, alkenylamino, cycloalkyl, cycloalkylalkyl, cycloalkyloxy, cycloalkylthio, cycloalkylamino, aryl, aryloxy, arylthio, arylamino, arylalkyl, arylalkoxy, arylalkylthio and arylalkylamino, $R^3$ represents an in each case optionally substituted radical from the group consisting of alkyl, alkoxy, alkenyl, alkinyl, cycloalkyl, cycloalkylalkyl, aryl and arylalkyl, $R^4$ represents hydrogen, cyano, halogen or optionally substituted alkyl, $R^5$ represents hydrogen, cyano, halogen or optionally substituted alkyl, and salts of compounds of the formula (I).

The general formula (I) is the sum of the compounds defined by the general formulae (IA) and (IB) below.

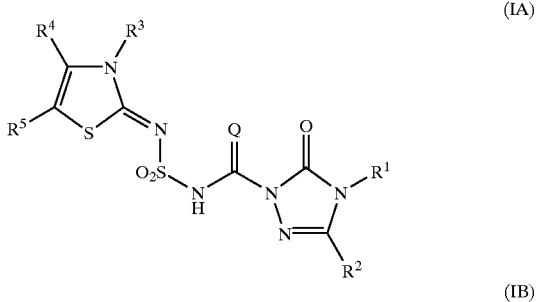

(IA)

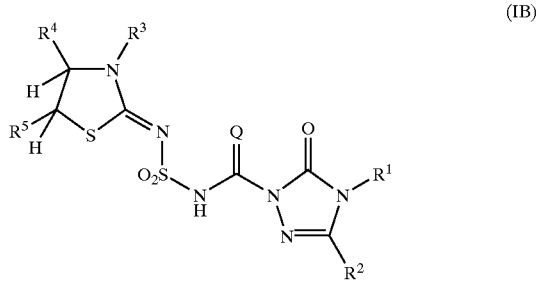

(IB)

In the general formulae (IA) and (IB), Q, $R^1$, $R^2$, $R^3$, $R^4$ and $R^5$ each have the meanings given above in the definition of the compounds of the general formula (I). If in the compounds of the formula (IB) $R^4$ and $R^5$ are both different from hydrogen, cis/trans isomerism may occur; the invention embraces in each case both isomers and cis/trans mixtures of any isomer ratio.

The novel compounds of the general formula (I) are obtained when (a) chlorosulphonylamino(thio)carbonyltriazolinones of the general formula (III)

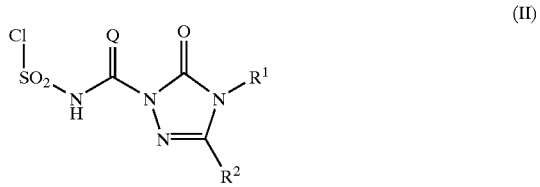

(II)

in which

Q, $R^1$ and $R^2$ are each as defined above, are reacted with iminothiazoli(di)nes of the general formula (III)

(III)

in which $R^3$, $R^4$ and $R^5$ are each as defined above,

-or with acid adducts of compounds of the general formula (III)-, if appropriate in the presence of a reaction auxiliary and if appropriate in the presence of a diluent, and, if appropriate, the resulting compounds of the formula (I) are converted by customary methods into salts, or when (b) triazolinones of the general formula (IV)

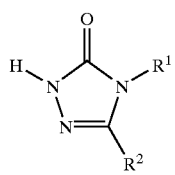  (IV)

in which
R¹ and R² are each as defined above,
are reacted with chlorosulphonyl iso(thio)cyanate of the general formula (V)

Cl—SO₂—N=C=Q  (V)

in which
Q is as defined above,
if appropriate in the presence of a reaction auxiliary and if appropriate in the presence of a diluent,
and the resulting chlorosulphonylamino(thio)carbonyltriazolinones of the general formula (II)

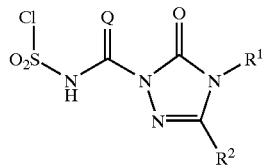  (II)

in which
Q, R¹ and R² are each as defined above,
are reacted with iminothiazoli(di)nes of the general formula (III)

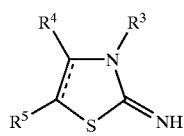  (III)

in which
R³, R⁴ and R⁵ are each as defined above,
if appropriate in the presence of a reaction auxiliary and if appropriate in the presence of a diluent,
and, if appropriate, the resulting compounds of the formula (I) are converted by customary methods into salts.

Further possible preparation methods for the compounds of the general formula (I) according to the invention are listed below, Q, R¹, R², R³, R⁴ and R⁵ being in each case as defined above.

(c) Reaction of triazolinone derivatives of the general formula (VI)

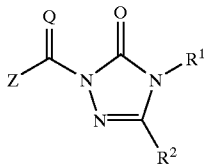  (VI)

in which
Q, R¹ and R² are each as defined above and
Z represents halogen, alkoxy, aralkoxy or aryloxy,
with aminosulphonyliminothiazoli(di)nes of the general formula (VII)

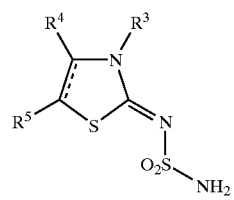  (VII)

in which
R³, R⁴ and R⁵ are each as defined above,
if appropriate in the presence of an acid acceptor and if appropriate in the presence of a diluent, (d) reaction of triazolinones of the general formula (IV)

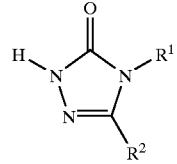  (IV)

in which
R¹ and R² are each as defined above,
with sulphonamide derivatives of the general formula (IX)

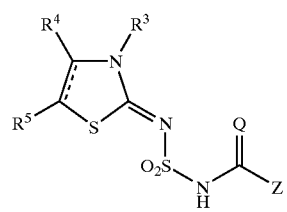  (IX)

in which
Q, R³, R⁴ and R⁵ are each as defined above and
Z represents halogen, alkoxy, aralkoxy or aryloxy,
if appropriate in the presence of an acid acceptor and if appropriate in the presence of a diluent.

The novel compounds of the general formula (I) have strong herbicidal activity.

Furthermore, the following applies to the definitions in formula (I):

Q preferably represents oxygen or sulphur.

R¹ preferably represents hydrogen, amino, $C_1$–$C_6$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents in each case optionally fluorine-, chlorine- and/or bromine-substituted $C_2$–$C_6$-alkenyl or $C_2$–$C_6$-alkinyl, represents $C_1$–$C_6$-alkyloxy or $C_2$–$C_6$-alkenyloxy, represents in each case optionally fluorine- and/or chlorine-substituted $C_1$–$C_6$-alkylamino, di-($C_1$–$C_4$-alkyl)-amino or $C_1$–$C_4$-alkanoylamino, represents in each case optionally fluorine-, chlorine-, bromine- and/or $C_1$–$C_4$-alkyl-substituted $C_3$–$C_6$-cycloalkyl or $C_3$–$C_6$-cycloalkyl-$C_1$–$C_4$-alkyl, or represents in each case optionally fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl or phenyl-$C_1$–$C_4$-alkyl.

$R^2$ preferably represents hydrogen, cyano, fluorine, chlorine, bromine, iodine, represents in each case optionally fluorine-, chlorine-, bromine-, cyano-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl- or $C_3$–$C_6$-cycloalkyl-substituted alkyl, alkoxy, alkylthio, alkylsulphinyl, alkylsulphonyl, alkylamino or dialkylamino having in each case 1 to 6 carbon atoms in the alkyl groups, represents in each case optionally fluorine-, chlorine- and/or bromine-substituted alkenyl, alkenyloxy, alkenylthio or alkenylamino having in each case 2 to 6 carbon atoms in the alkenyl groups, represents alkinyl having 2 to 6 carbon atoms, represents in each case optionally fluorine-, chlorine-, bromine-, cyano- and/or $C_1$–$C_4$-alkyl-substituted cycloalkyl, cycloalkylalkyl, cycloalkyloxy, cycloalkylthio or cycloalkylamino having in each case 3 to 6 carbon atoms in the cycloalkyl groups and optionally 1 to 3 carbon atoms in the alkyl moiety, represents in each case optionally fluorine-, chlorine-, bromine-, cyano-, nitro-, $C_1$–$C_4$-alkyl-, trifluoromethyl-, $C_1$–$C_4$-alkoxy, difluoromethoxy- or trifluoromethoxy-substituted phenyl, phenoxy, phenylthio, phenylamino, benzyl, benzyloxy, benzylthio or benzylamino.

$R^3$ preferably represents optionally cyano-, carboxyl-, carbamoyl-, fluorine-, chlorine-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted alkyl having 1 to 6 carbon atoms, represents optionally cyano-, fluorine-, chlorine- or $C_1$–$C_4$-alkoxy-substituted alkoxy having 1 to 6 carbon atoms, represents in each case optionally cyano-, carboxyl-, carbamoyl-, fluorine-, chlorine-, bromine-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted alkenyl or alkinyl having in each case 2 to 6 carbon atoms, represents in each case optionally cyano-, carboxyl-, carbamoyl-, fluorine-, chlorine-, bromine-, $C_1$–$C_4$-alkyl-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted cycloalkyl or cycloalkylalkyl having in each case 3 to 6 carbon atoms in the cycloalkyl groups and optionally 1 to 3 carbon atoms in the alkyl moiety, or represents phenyl or benzyl, each of which is optionally substituted by nitro, cyano, carboxyl, carbamoyl, fluorine, chlorine, bromine, or by (in each case optionally fluorine- and/or chlorine-substituted substituted) $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl.

$R^4$ preferably represents hydrogen, cyano, fluorine, chlorine, bromine or optionally fluorine- and/or chlorine-substituted alkyl having 1 to 4 carbon atoms.

$R^5$ preferably represents hydrogen, cyano, fluorine, chlorine, bromine or optionally fluorine- and/or chlorine-substituted alkyl having 1 to 4 carbon atoms.

The invention furthermore preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-amnmonium, tetra-($C_1$–$C_4$-alkyl)-ammonium, tri-($C_1$–$C_4$-alkyl)-sulphonium, $C_5$– or $C_6$-cycloalkyl-ammonium and di-($C_1$–$C_2$-alkyl)-benzyl-ammonium salts of compounds of the formula (I), in which Q, $R^1$, $R^2$, $R^3$, $R^4$ and $R^5$ each have the meanings given above as being preferred.

A preferred group are the compounds of the general formula (IA), in which Q, $R^1$, $R^2$, $R^3$, $R^4$ and $R^5$ each have the meanings given above as being preferred.

A further preferred group are the compounds of the general formula (IB) in which Q, $R^1$, $R^2$, $R^3$, $R^4$ and $R^5$ each have the meanings given above as being preferred.

Q particularly preferably represents oxygen or sulphur.

$R^1$ particularly preferably represents in each case optionally fluorine-, chlorine-, cyano-, methoxy- or ethoxy-substituted methyl, ethyl, n- or i-propyl, represents in each case optionally fluorine-, chlorine- or bromine-substituted ethenyl, propenyl, butenyl, propinyl or butinyl, represents methoxy, ethoxy, n- or i-propoxy or represents allyloxy, represents methylamino, ethylamino, n- or i-propylamino, dimethylamino or diethylamino, or represents optionally fluorine-, chlorine-, bromine-, methyl- or ethyl-substituted cyclopropyl.

$R^2$ particularly preferably represents chlorine or bromine, represents in each case optionally fluorine-, chlorine-, bromine-, cyano-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, n-, i-, s- or t-butylsulphinyl, n-, i-, s- or t-butylsulphonyl, methylamino, ethylamino, n- or i-propylamino, n-, i-, s- or t-butylamino, dimethylamino or diethylamino, represents in each case optionally fluorine-, chlorine- and/or bromine-substituted ethenyl, propenyl, butenyl, ethenyloxy, propenyloxy, butenyloxy, propenylthio, butenylthio, propenylamino or butenylamino, represents propinyl, butinyl, propinyloxy, butinyloxy, propinylthio or butinylthio, represents in each case optionally fluorine-, chlorine-, bromine-, cyano- and/or methyl-substituted cyclopropyl, cyclobutyl, cyclopentyl, cyclohexyl, cyclohexenyl, cyclopropyloxy, cyclobutyloxy, cyclopentyloxy, cyclohexyloxy, cyclopropylthio, cyclobutylthio, cyclopentylthio or cyclohexylthio, represents in each case optionally fluorine-, chlorine-, bromine-, cyano-, methyl-, trifluoromethyl-, methoxy-, difluoromethoxy- or trifluoromethoxy-substituted phenyl, phenoxy, phenylthio, phenylamino, benzyl, benzyloxy, benzylthio or benzylamino.

$R^3$ particularly preferably represents in each case optionally cyano-, carboxyl-, carbamoyl-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethyl-amino-carbonyl-substituted methyl, ethyl, n- or i-propyl, n-, i-, s- or t-butyl, represents in each case optionally cyano-, fluorine-, chlorine-, methoxy- or ethoxy-substituted methoxy, ethoxy, n- or i-propoxy, represents in each case optionally cyano-, carboxyl-, carbamoyl-, fluorine-, chlorine-, bromine-, acetyl-, propionyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethyl-amino-carbonyl-substituted ethenyl, propenyl, butenyl, ethinyl, propinyl or butinyl, represents in each case optionally cyano-, carboxyl-, carbamoyl-, fluorine-, chlorine-, bromine-, methyl-, ethyl-, n- or i-propyl-, n-, i-, s- or t-butyl-, acetyl-, propionyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethyl-amino-carbonyl-substituted cyclopropyl, cyclobutyl, cyclopentyl, cyclohexyl, cyclopropylmethyl, cyclobutylmethyl, cyclopentylmethyl or cyclohexylmethyl, or represents phenyl or benzyl each of which is optionally substituted by nitro, cyano, carboxyl, carbamoyl, fluorine, chlorine, bromine, or by (in each case optionally fluorine- and/or chlorine-substituted substituted) methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl.

$R^4$ particularly preferably represents hydrogen, cyano, fluorine, chlorine, bromine or optionally fluorine- and/or chlorine-substituted methyl, ethyl, n- or i-propyl.

$R^5$ particularly preferably represents hydrogen, cyano, fluorine, chlorine, bromine or optionally fluorine- and/or chlorine-substituted methyl, ethyl, n- or i-propyl.

The general or preferred radical definitions listed above apply both to the end products of the formula (I) and, correspondingly, to the starting materials and intermediates required in each case for the preparation. These radical definitions can be combined with one another as desired, i.e. including combinations between the given ranges of preferred compounds.

Even if not explicitly mentioned, the hydrocarbon radicals mentioned in the radical definitions, such as alkyl, alkenyl or alkinyl, can be straight-chain or branched, including in combinations with hetero atoms, such as in alkoxy, alkylthio or alkyl-amino.

Halogen generally represents fluorine, chlorine, bromine or iodine, preferably fluorine, chlorine or bromine, in particular fluorine or chlorine.

Using, for example, 2-chlorosulphonylaminocarbonyl-5-ethoxy-4-methyl-2,4-dihydro-3H-1,2,4-triazol-3-one and 3-ethoxy-3H-thiazol-2-ylideneamine as starting materials, the course of the reaction in the process (a) according to the invention can be illustrated by the following equation:

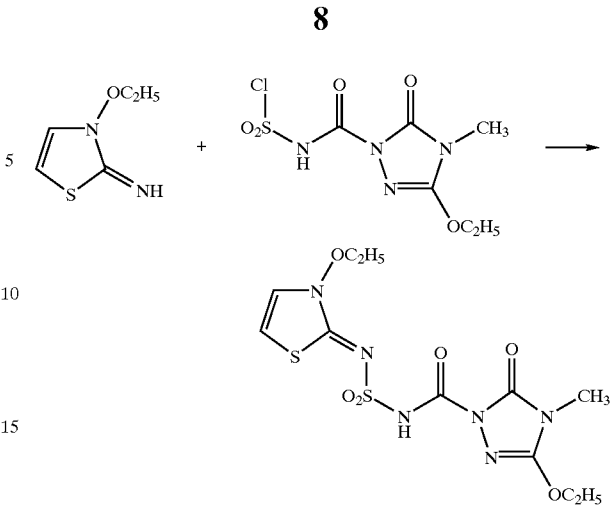

Using, for example, 4-ethyl- 5-methylthio-2,4-dihydro-3H-1,2,4-triazol-3-one and chlorosulphonyl isocyanate and then 3-(2-chloro-ethyl)-thiazolin-2-ylideneamine as starting materials, the course of the reaction of the process (b) according to the invention can be illustrated by the following equation:

The formula (II) provides a general definition of the chlorosulphonylamino(thio)-carbonyltriazolinones to be used as starting materials in the process (a) according to the invention for preparing compounds of the formula (I). In the formula (II), Q, $R^1$ and $R^2$ each preferably or in particular have those meanings which have already been mentioned above, in connection with the description of the compounds of the formula (I) according to the invention, as being preferred or as being particularly preferred for Q, $R^1$ and $R^2$.

The starting materials of the general formula (II) are known and/or can be prepared by processes known per se (cf. WO 94/08979, WO 95/27703).

The formula (III) provides a general definition of the iminothiazoli(di)nes to be used as starting materials in the processes (a) and (b) according to the invention; the compounds of the formula (III) can also be referred to as thiazol(in)ylideneamines. In the formula (III), $R^3$, $R^4$ and $R^5$ each preferably or in particular have those meanings which have already been mentioned above, in connection with the description of the compounds of the formula (I) according to the invention, as being preferred or as being particularly preferred for $R^3$, $R^4$ and $R^5$.

The starting materials of the general formula (III) are known and/or can be prepared by processes known per se (cf. WO 93/00336/EP 592676).

The formula (IV) provides a general definition of the triazolinones to be used as starting materials in the process (b) according to the invention for preparing compounds of the formula (I). In the formula (IV), $R^1$ and $R^2$ each preferably or in particular have those meanings which have already been mentioned, in connection with the description of the compounds of the formula (I) according to the invention, as being preferred or as being particularly preferred for $R^1$ and $R^2$.

The starting materials of the formula (IV) are known and/or can be prepared by processes known per se (cf. EP 283 876, EP 294666, EP 301 946, EP 298 371, EP 341 489, EP 399 294, EP 398 096, EP 422 469, EP 425 948, EP 431 291, EP 477 646).

The processes (a) and (b) according to the invention for preparing the novel compounds of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitrites, such as, for example, aceto-nitrile and propionitrile, amides, such as, for example, dimethylformamide, dimethylacetamide and N-methylpyrrolidone, and also dimethylsulphoxide, tetramethylene sulphone and hexamethylphosphoric triamide.

Suitable acid acceptors for use in the processes (a) and (b) according to the invention are all acid binders customarily used for reactions of this type. Preference is given to alkali metal hydroxides, such as, for example, sodium hydroxide and potassium hydroxide, alkaline earth metal hydroxides, such as, for example, calcium hydroxide, alkali metal carbonates and alkoxides, such as sodium carbonate and potassium carbonate, sodium tert-butoxide and potassium tert-butoxide, furthermore basic nitrogen compounds, such as trimethylamine, triethylamine, tripropylamine, tributylamine, disobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethy-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo[2,2,2]-octane (DABCO).

In the processes (a) and (b) according to the invention, the reaction temperatures can be varied within a relatively wide range. In general, the processes are carried out at temperatures between −20° C. and +80° C., preferably at temperatures between 0° and +50° C.

The processes (a) and (b) according to the invention are generally carried out under atmospheric pressure. However, it is also possible to operate under elevated or reduced pressure.

For carrying out the processes (a) and (b) according to the invention, the starting materials required in each case are generally employed in approximately equimolar amounts. However, it is also possible to use a relatively large excess of one of the compounds used in each case. The reactions are generally carried out in a suitable diluent in the presence of an acid acceptor, and the reaction mixture is stirred for a plurality of hours at the temperature required in each case. Work-up in the processes (a) and (b) according to the invention is in each case carried out by customary methods (cf. the Preparation Examples).

If appropriate, salts can be prepared from the compounds of the general formula (I) according to the invention. Such salts are obtained in a simple manner by customary methods for forming salts, for example by dissolving or dispersing a compound of the formula (I) in a suitable solvent, such as, for example, methylene chloride, acetone, tert-butyl methyl ether or toluene, and adding a suitable base. The salts can then—if appropriate after prolonged stirring—be isolated by concentration or filtration with suction.

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera Aegilops, Phalaris.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on above-ground parts of plants; some of them are also suitable for the selective control of monocotyledonous and dicotyledonous weeds in the monocotyledonous and dicotyledonous crops, both by the pre-emergence and by the post-emergence method.

To a certain extent, the compounds of the formula (I) according to the invention also have fungicidal activity, for example against oomycetes and against fusaria.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop (-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyrT(meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

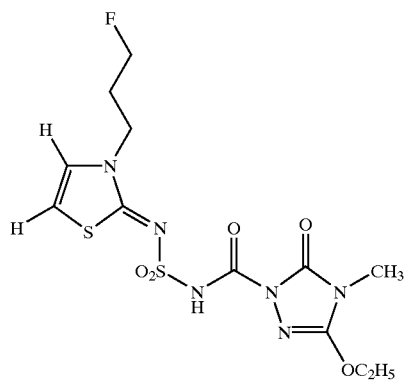

(Process (b))

At room temperature (about 20° C.), a solution of 1.7 g (10 mMol) of 3-(3-fluoro-propyl)-3H-thiazol-2-ylideneamine and 1.2 g (12 mMol) of triethylamine in 5 ml of methylene chloride is added dropwise with stirring to a mixture of 1.5 g (10 mMol) of 5-ethoxy-4-methyl-2,4-dihydro-3H-1,2,4-triazol-3-one, 1.5 g (10 mMol) of chlorosulphonyl isocyanate and 50 ml of methylene chloride. The reaction mixture is stirred at room temperature for about 30 minutes and then washed with water, dried with sodium sulphate and filtered. The filtrate is concentrated under waterpump vacuum, the residue is digested with isopropanol and the resulting crystalline product is isolated by filtration with suction.

This gives 2.2 g (54% of theory) of 2-[(3-fluoro-propyl)-3H-thiazol-2-ylideneaminosulphonylaminocarbonyl]-5-ethoxy-4-methyl-2,4-dihydro-3H-1,2,4-triazol-3-one of melting point 178° C.

Analogously to Preparation Example 1, and in accordance with the general description of the preparation processes according to the invention, it is also possible to prepare, for example, the compounds of the formula (I)—or of the formulae (IA) and (IB)—listed in Table 1 below.

TABLE 1

Examples of compounds of the formula (I) - of formulae (IA) and (IB)

| Ex. No. | General formula | Q | $R^1$ | $R^2$ | $R^3$ | $R^4$ | $R^5$ | Physical data |
|---|---|---|---|---|---|---|---|---|
| 2 | (IA) | O | $CH_3$ | $C_3H_7$-n | $C_3H_7$-n | H | H | |
| 3 | (IA) | O | $CH_3$ | $SCH_3$ | $C_3H_7$-n | H | H | |
| 4 | (IA) | O | $CH_3$ | $SC_2H_5$ | $C_3H_7$-n | H | H | |
| 5 | (IA) | O | $CH_3$ | $OCH_3$ | $C_3H_7$-n | H | H | |
| 6 | (IA) | O | $CH_3$ | $OC_2H_5$ | $C_3H_7$-n | H | H | |
| 7 | (IA) | O | $CH_3$ | $OCH_2CF_3$ | $C_3H_7$-n | H | H | |
| 8 | (IA) | O | $CH_3$ | $OC_3H_7$-n | $C_3H_7$-n | H | H | |
| 9 | (IA) | O | $CH_3$ | $OC_3H_7$-i | $C_3H_7$-n | H | H | |
| 10 | (IA) | O | $C_2H_5$ | $OCH_3$ | $C_3H_7$-n | H | H | |
| 11 | (IA) | O | cyclopropyl | $C_3H_7$-i | $C_3H_7$-n | H | H | |
| 12 | (IA) | O | $CH_3$ | $N(CH_3)_2$ | $CH_3$ | H | H | |
| 13 | (IA) | O | $CH_3$ | $SC_2H_5$ | $CH_3$ | H | H | |
| 14 | (IA) | O | $CH_3$ | $OCH_3$ | $CH_3$ | H | H | |
| 15 | (IA) | O | $CH_3$ | $OC_2H_5$ | $CH_3$ | H | H | m.p.: 163° C. |
| 16 | (IA) | O | $CH_3$ | $OC_3H_7$-n | $CH_3$ | H | H | |
| 17 | (IA) | O | $CH_3$ | $OC_3H_7$-i | $CH_3$ | H | H | |
| 18 | (IA) | O | $CH_3$ | $OC_4H_9$-n | $CH_3$ | H | H | |
| 19 | (IA) | O | $C_2H_5$ | $OCH_3$ | $CH_3$ | H | H | |
| 20 | (IA) | O | $C_2H_5$ | $OC_2H_5$ | $CH_3$ | H | H | |

TABLE 1-continued

Examples of compounds of the formula (I) - of formulae (IA) and (IB)

| Ex. No. | General formula | Q | R¹ | R² | R³ | R⁴ | R⁵ | Physical data |
|---|---|---|---|---|---|---|---|---|
| 21 | (IA) | O | cyclopropyl | $OC_3H_7$-n | $CH_3$ | H | H | |
| 22 | (IA) | O | cyclopropyl | $OC_3H_7$-i | $CH_3$ | H | H | |
| 23 | (IA) | O | cyclopropyl | H | $C_3H_7$-n | H | H | |
| 24 | (IA) | O | cyclopropyl | $N(CH_3)_2$ | $C_3H_7$-n | H | H | |
| 25 | (IA) | O | cyclopropyl | $SCH_3$ | $C_3H_7$-n | H | H | |
| 26 | (IA) | O | cyclopropyl | $SC_2H_5$ | $C_3H_7$-n | H | H | |
| 27 | (IA) | O | cyclopropyl | $SCH_2CH=CH_2$ | $C_3H_7$-n | H | H | |
| 28 | (IA) | O | cyclopropyl | $SCH_2C{\equiv}CH$ | $C_3H_7$-n | H | H | |
| 29 | (IA) | O | cyclopropyl | $OCH_3$ | $C_3H_7$-n | H | H | |
| 30 | (IA) | O | cyclopropyl | $OC_2H_5$ | $C_3H_7$-n | H | H | |
| 31 | (IA) | O | cyclopropyl | $OCH_2CF_3$ | $C_3H_7$-n | H | H | |
| 32 | (IA) | O | cyclopropyl | $OC_3H_7$-n | $C_3H_7$-n | H | H | |
| 33 | (IA) | O | cyclopropyl | $OC_3H_7$-i | $C_3H_7$-n | H | H | |

TABLE 1-continued

Examples of compounds of the formula (I) - of formulae (IA) and (IB)

| Ex. No. | General formula | Q | $R^1$ | $R^2$ | $R^3$ | $R^4$ | $R^5$ | Physical data |
|---|---|---|---|---|---|---|---|---|
| 34 | (IA) | O | cyclopropyl-CH$_2$- | -CH$_2$-O-cyclopropyl | C$_3$H$_7$-n | H | H | |
| 35 | (IA) | O | cyclopropyl-CH$_2$- | OC$_4$H$_9$-n | C$_3$H$_7$-n | H | H | |
| 36 | (IA) | O | OCH$_3$ | OC$_3$H$_7$-n | C$_3$H$_7$-n | H | H | |
| 37 | (IA) | O | OC$_2$H$_5$ | OC$_2$H$_5$ | C$_3$H$_7$-n | H | H | |
| 38 | (IA) | O | CH$_3$ | CH$_3$ | C$_3$H$_7$-n | H | H | |
| 39 | (IA) | O | CH$_3$ | C$_2$H$_5$ | C$_3$H$_7$-n | H | H | |
| 40 | (IA) | O | CH$_3$ | CH$_2$OCH$_3$ | C$_3$H$_7$-n | H | H | |
| 41 | (IA) | O | CH$_3$ | cyclopropyl-CH$_2$- | C$_3$H$_7$-n | H | H | |
| 42 | (IA) | O | CH$_3$ | C$_3$H$_7$-i | C$_3$H$_7$-n | H | H | |
| 43 | (IA) | O | CH$_3$ | C$_4$H$_9$-n | C$_3$H$_7$-n | H | H | |
| 44 | (IA) | O | CH$_3$ | H | C$_3$H$_7$-n | H | H | |
| 45 | (IA) | O | CH$_3$ | N(CH$_3$)$_2$ | C$_3$H$_7$-n | H | H | |
| 46 | (IA) | O | CH$_3$ | CH≡C-CH$_2$-S-CH$_3$ (propargyl-S-CH$_3$, as drawn) | C$_3$H$_7$-n | H | H | |
| 47 | (IA) | O | CH$_3$ | HC≡C-CH$_2$-S-CH$_3$ | C$_3$H$_7$-n | H | H | |
| 48 | (IA) | O | CH$_3$ | CH$_3$-O-CH$_2$-cyclopropyl | C$_3$H$_7$-n | H | H | |
| 49 | (IA) | O | C$_2$H$_5$ | OC$_2$H$_5$ | C$_3$H$_7$-n | H | H | |
| 50 | (IA) | O | cyclopropyl-CH$_2$- | C$_2$H$_5$ | C$_3$H$_7$-n | H | H | |
| 51 | (IA) | O | cyclopropyl-CH$_2$- | CH$_3$-CH=CH-CH$_2$- | C$_3$H$_7$-n | H | H | |
| 52 | (IA) | O | cyclopropyl-CH$_2$- | cyclopropyl-CH$_2$- | C$_3$H$_7$-n | H | H | |

TABLE 1-continued

Examples of compounds of the formula (I) - of formulae (IA) and (IB)

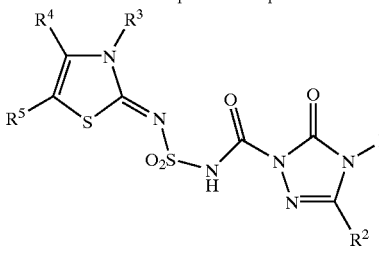

| Ex. No. | General formula | Q | R¹ | R² | R³ | R⁴ | R⁵ | Physical data |
|---|---|---|---|---|---|---|---|---|
| 53 | (IA) | O | CH₃ | 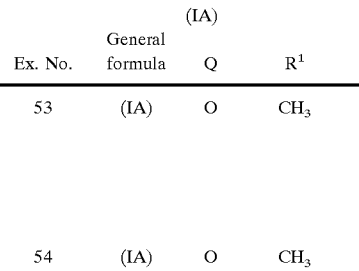 | C₃H₇-n | H | H | |
| 54 | (IA) | O | CH₃ | OC₄H₉-n | C₃H₇-n | H | H | |
| 55 | (IA) | O |  | C₃H₇-n | C₃H₇-n | H | H | |
| 56 | (IA) | O |  | CH₂OCH₃ | C₃H₇-n | H | H | |
| 57 | (IA) | O | CH₃ | CH₃ | CH₃ | H | H | |
| 58 | (IA) | O | CH₃ | 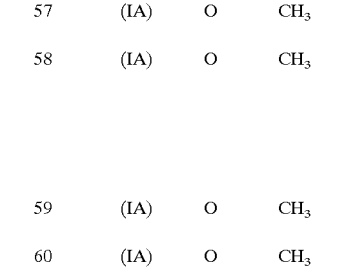 | CH₃ | H | H | |
| 59 | (IA) | O | CH₃ | CH₂OCH₃ | CH₃ | H | H | |
| 60 | (IA) | O | CH₃ | 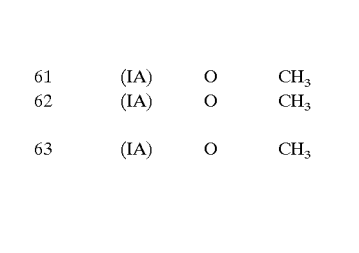 | CH₃ | H | H | |
| 61 | (IA) | O | CH₃ | C₃H₇-i | CH₃ | H | H | |
| 62 | (IA) | O | CH₃ | C₄H₉-n | CH₃ | H | H | |
| 63 | (IA) | O | CH₃ | 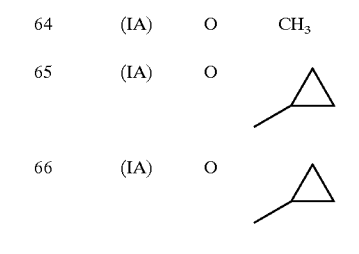 | CH₃ | H | H | |
| 64 | (IA) | O | CH₃ | OCH₂CF₃ | CH₃ | H | H | |
| 65 | (IA) | O |  | CH₃ | CH₃ | H | H | |
| 66 | (IA) | O | 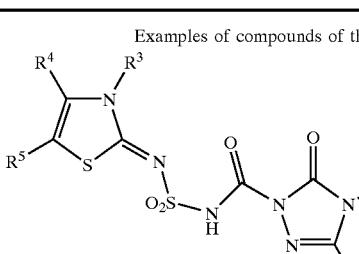 | C₂H₅ | CH₃ | H | H | |
| 67 | (IA) | O | 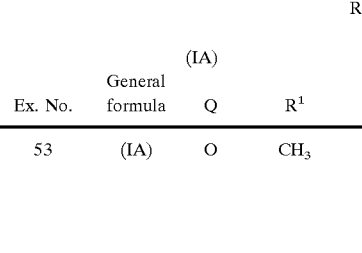 | CH₃H₇-n | CH₃ | H | H | |

TABLE 1-continued

Examples of compounds of the formula (I) - of formulae (IA) and (IB)

| Ex. No. | General formula | Q | R¹ | R² | R³ | R⁴ | R⁵ | Physical data |
|---|---|---|---|---|---|---|---|---|
| 68 | (IA) | O | cyclopropyl | CH₃-CH=CH-CH₂- | CH₃ | H | H | |
| 69 | (IA) | O | cyclopropyl | CH₂OCH₃ | CH₃ | H | H | |
| 70 | (IA) | O | cyclopropyl | cyclopropyl | CH₃ | H | H | |
| 71 | (IA) | O | cyclopropyl | C₃H₇-i | CH₃ | H | H | |
| 72 | (IA) | O | cyclopropyl | C₄H₉-n | CH₃ | H | H | |
| 73 | (IA) | O | cyclopropyl | H | CH₃ | H | H | |
| 74 | (IA) | O | cyclopropyl | N(CH₃)₂ | CH₃ | H | H | |
| 75 | (IA) | O | cyclopropyl | SCH₃ | CH₃ | H | H | |
| 76 | (IA) | O | cyclopropyl | SC₂H₅ | CH₃ | H | H | |
| 77 | (IA) | O | cyclopropyl | CH₂=CH-CH₂-S-CH₂- | CH₃ | H | H | |
| 78 | (IA) | O | cyclopropyl | HC≡C-CH₂-S-CH₂- | CH₃ | H | H | |
| 79 | (IA) | O | cyclopropyl | OCH₃ | CH₃ | H | H | |

TABLE 1-continued

Examples of compounds of the formula (I) - of formulae (IA) and (IB)

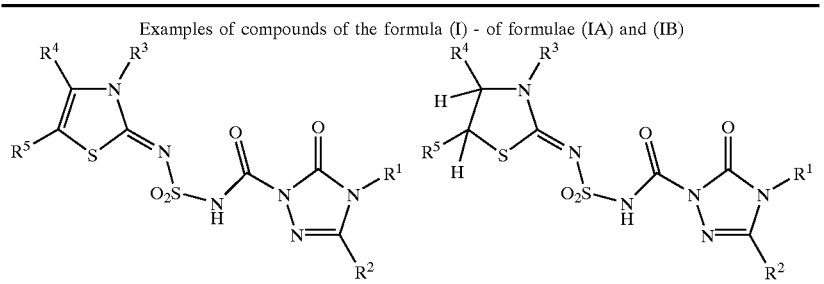

| Ex. No. | General formula | Q | R¹ | R² | R³ | R⁴ | R⁵ | Physical data |
|---|---|---|---|---|---|---|---|---|
| 80 | (IA) | O | cyclopropyl-CH₂ | $OC_2H_5$ | $CH_3$ | H | H | |
| 81 | (IA) | O | cyclopropyl-CH₂ | $CH_2OCH_3$ | $CH_3$ | H | H | |
| 82 | (IA) | O | cyclopropyl-CH₂ | cyclopropyl-CH₂-O- | $CH_3$ | H | H | |
| 83 | (IA) | O | cyclopropyl-CH₂ | $OC_4H_9$-n | $CH_3$ | H | H | |
| 84 | (IA) | O | $OCH_3$ | $C_3H_7$-n | $CH_3$ | H | H | |
| 85 | (IA) | O | $OC_2H_5$ | $C_2H_5$ | $CH_3$ | H | H | |
| 86 | (IA) | O | $CH_3$ | $CH_3$ | $C_2H_5$ | H | H | |
| 87 | (IA) | O | $CH_3$ | $C_2H_5$ | $C_2H_5$ | H | H | |
| 88 | (IA) | O | $CH_3$ | $C_3H_7$-n | $C_2H_5$ | H | H | |
| 89 | (IA) | O | $CH_3$ | $CH_3$-CH=CH-CH₂- | $C_2H_5$ | H | H | |
| 90 | (IA) | O | $CH_3$ | $CH_2OCH_3$ | $C_2H_5$ | H | H | |
| 91 | (IA) | O | $CH_3$ | cyclopropyl-CH₂ | $C_2H_5$ | H | H | |
| 92 | (IA) | O | $CH_3$ | $C_3H_7$-i | $C_2H_5$ | H | H | |
| 93 | (IA) | O | $CH_3$ | $C_4H_9$-n | $C_2H_5$ | H | H | |
| 94 | (IA) | O | $CH_3$ | H | $C_2H_5$ | H | H | |
| 95 | (IA) | O | $CH_3$ | $N(CH_3)_2$ | $C_2H_5$ | H | H | |
| 96 | (IA) | O | $CH_3$ | $CH_2=CH-CH_2-S-CH_2-$ | $C_2H_5$ | H | H | |
| 97 | (IA) | O | $CH_3$ | $HC\equiv C-CH_2-S-CH_2-$ | $C_2H_5$ | H | H | |
| 98 | (IA) | O | $CH_3$ | $OCH_3$ | $C_2H_5$ | H | H | |
| 99 | (IA) | O | $CH_3$ | $OC_2H_5$ | $C_2H_5$ | H | H | m.p.: 170° C. |
| 100 | (IA) | O | $CH_3$ | $OCH_2CF_3$ | $C_2H_5$ | H | H | |
| 101 | (IA) | O | $CH_3$ | $OC_3H_7$-n | $C_2H_5$ | H | H | |
| 102 | (IA) | O | $CH_3$ | $OC_3H_7$-i | $C_2H_5$ | H | H | |

TABLE 1-continued

Examples of compounds of the formula (I) - of formulae (IA) and (IB)

| Ex. No. | General formula | Q | R¹ | R² | R³ | R⁴ | R⁵ | Physical data |
|---------|-----------------|---|----|----|----|----|----|---------------|
| 103 | (IA) | O | CH₃ |  | C₂H₅ | H | H | |
| 104 | (IA) | O | C₂H₅ | OCH₃ | C₂H₅ | H | H | |
| 105 | (IA) | O | C₂H₅ | OC₂H₅ | C₂H₅ | H | H | |
| 106 | (IA) | O |  | CH₃ | C₂H₅ | H | H | |
| 107 | (IA) | O |  | C₂H₅ | C₂H₅ | H | H | |
| 108 | (IA) | O |  | C₃H₇-n | C₂H₅ | H | H | |
| 109 | (IA) | O |  | CH₂OCH₃ | C₂H₅ | H | H | |
| 110 | (IA) | O | 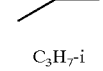 |  | C₂H₅ | H | H | |
| 111 | (IA) | O |  | C₃H₇-i | C₂H₅ | H | H | |
| 112 | (IA) | O |  | C₄H₉-n | C₂H₅ | H | H | |
| 113 | (IA) | O |  | H | C₂H₅ | H | H | |
| 114 | (IA) | O |  | SCH₃ | C₂H₅ | H | H | |
| 115 | (IA) | O | 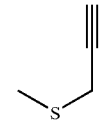 |  | C₂H₅ | H | H | |
| 116 | (IA) | O |  | OCH₃ | C₂H₅ | H | H | |
| 117 | (IA) | O |  | OC₂H₅ | C₂H₅ | H | H | |

TABLE 1-continued

Examples of compounds of the formula (I) - of formulae (IA) and (IB)

| Ex. No. | General formula | Q | R¹ | R² | R³ | R⁴ | R⁵ | Physical data |
|---|---|---|---|---|---|---|---|---|
| 118 | (IA) | O | cyclopropyl | OC$_3$H$_7$-n | C$_2$H$_5$ | H | H | |
| 119 | (IA) | O | cyclopropyl | OC$_3$H$_7$-i | C$_2$H$_5$ | H | H | |
| 120 | (IA) | O | cyclopropyl | OC$_4$H$_9$-n | C$_2$H$_5$ | H | H | |
| 121 | (IA) | O | C$_2$H$_5$ | OC$_2$H$_5$ | C$_2$H$_5$ | H | H | |
| 122 | (IA) | O | CH$_3$ | C$_2$H$_5$ | CH$_3$ | H | H | |
| 123 | (IA) | O | OCH$_3$ | OCH$_3$ | (CH$_2$)$_3$F | H | H | m.p.: 170° C. |
| 124 | (IA) | O | CH$_3$ | OCH$_3$ | (CH$_2$)$_3$F | H | H | m.p.: 189° C. |
| 125 | (IA) | O | CH$_3$ | OC$_3$H$_7$-i | (CH$_2$)$_3$F | H | H | m.p.: 170° C. |
| 126 | (IA) | O | CH$_3$ | OC$_3$H$_7$-n | (CH$_2$)$_3$F | H | H | m.p.: 143° C. |
| 127 | (IA) | O | CH$_3$ | OCH$_2$CF$_3$ | (CH$_2$)$_3$F | H | H | m.p.: 152° C. |
| 128 | (IA) | O | CH$_3$ | SCH$_3$ | (CH$_2$)$_3$F | H | H | m.p.: 165° C. |
| 129 | (IA) | O | cyclopropyl | OCH$_3$ | (CH$_2$)$_3$F | H | H | m.p.: 163° C. |
| 130 | (IA) | O | cyclopropyl | OC$_2$H$_5$ | (CH$_2$)$_3$F | H | H | m.p.: 180° C. |
| 131 | (IA) | O | cyclopropyl | OC$_3$H$_7$-i | (CH$_2$)$_3$F | H | H | m.p.: 154° C. |
| 132 | (IA) | O | cyclopropyl | OC$_3$H$_7$-n | (CH$_2$)$_3$F | H | H | m.p.: 175° C. |
| 133 | (IA) | O | cyclopropyl | OCH$_2$CF$_3$ | (CH$_2$)$_3$F | H | H | m.p.: 112° C. |
| 134 | (IA) | O | CH$_3$ | CH$_3$ | (CH$_2$)$_3$F | H | H | m.p.: 177° C. |
| 135 | (IA) | O | CH$_3$ | C$_2$H$_5$ | (CH$_2$)$_3$F | H | H | m.p.: 153° C. |
| 136 | (IA) | O | CH$_3$ | C$_3$H$_7$-n | (CH$_2$)$_3$F | H | H | m.p.: 142° C. |
| 137 | (IA) | O | OC$_2$H$_5$ | C$_2$H$_5$ | (CH$_2$)$_3$F | H | H | m.p.: 160° C. |
| 138 | (IA) | O | OCH$_3$ | SCH$_3$ | (CH$_2$)$_3$F | H | H | m.p.: 162° C. |
| 139 | (IA) | O | H$_3$C–C(=N–)–C$_4$H$_9$-i | CH$_3$ | (CH$_2$)$_3$F | H | H | m.p.: 150° C. |
| 140 | (IA) | O | NH$_2$ | C$_3$H$_7$-i | (CH$_2$)$_3$F | H | H | m.p.: 140° C. |
| 141 | (IA) | O | CH$_3$ | OC$_2$H$_5$ | (CH$_2$)$_2$CN | H | H | m.p.: 198° C. |
| 142 | (IA) | O | CH$_3$ | OC$_2$H$_5$ | (CH$_2$)$_2$CF$_3$ | H | H | m.p.: 183° C. |
| 143 | (IA) | O | CH$_3$ | OC$_2$H$_5$ | C$_5$H$_{11}$-n | H | H | m.p.: 134° C. |
| 144 | (IA) | O | CH$_3$ | OCH$_3$ | (CH$_2$)$_2$CF$_3$ | H | H | m.p.: 189° C. |
| 145 | (IA) | O | CH$_3$ | OCH$_3$ | (CH$_2$)$_2$CN | H | H | m.p.: 190° C. |

TABLE 1-continued

Examples of compounds of the formula (I) - of formulae (IA) and (IB)

| Ex. No. | General formula (IA) | Q | R¹ | R² | R³ | R⁴ | R⁵ | Physical data |
|---------|----------------------|---|------|---------|----------------|----|----|---------------|
| 146 | (IA) | O | CH₃ | OCH₃ | C₅H₁₁-n | H | H | m.p.: 179° C. |
| 147 | (IA) | O | cyclopropyl | OC₂H₅ | (CH₂)₂CF₃ | H | H | m.p.: 171° C. |
| 148 | (IA) | O | cyclopropyl | OC₂H₅ | (CH₂)₂CN | H | H | m.p.: 188° C. |
| 149 | (IA) | O | cyclopropyl | OC₂H₅ | C₅H₁₁-n | H | H | m.p.: 146° C. |
| 150 | (IB) | O | CH₃ | OCH₃ | (CH₂)₃F | H | H | |
| 151 | (IB) | O | CH₃ | OC₂H₅ | (CH₂)₃F | H | H | |
| 152 | (IB) | O | cyclopropyl | OC₃H₇-i | (CH₂)₃F | H | H | |
| 153 | (IB) | O | CH₃ | OCH₃ | (CH₂)₂CF₃ | H | H | |
| 154 | (IB) | O | CH₃ | OC₂H₅ | (CH₂)₂CF₃ | H | H | |
| 155 | (IB) | O | cyclopropyl | OC₃H₇-i | (CH₂)₂CF₃ | H | H | |

Note
The radical R¹ in Example 139 (the size of which has been reduced considerably) has the following meaning

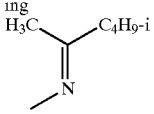

USE EXAMPLES

Example A

Pre-emergence test

| Solvent: | 5 parts by weight of acetone |
|----------|------------------------------|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liters of water per hectare.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 29, 30, 33, 51, 56, 124, 125, 130 and 131 show very strong activity against weeds, and some are tolerated well by crop plants, such as, for example, maize and sugar beet.

TABLE A

Pre-emergence test/greenhouse

| Active compound of Preparation Example No. | Application rate (g of a.i./ha) | Maize | Sugar beet | Echino-chloa | Setaria | Ama-ranthus | Matri-caria | Vero-nica |
|---|---|---|---|---|---|---|---|---|
| (124) | 125 | 0 | 0 | 90 | 95 | 70 | 100 | 95 |

| Active compound of Preparation Example No. | Application rate (g of a.i./ha) | Digi-taria | Echino-chloa | Ama-ranthus | Cheno-podium | Matri-caria | Vero-nica |
|---|---|---|---|---|---|---|---|
| (29) | 125 | — | 95 | 100 | 100 | 95 | 100 |
| (30) | 125 | 90 | 95 | 100 | 100 | 100 | 100 |
| (33) | 125 | — | 80 | 100 | 100 | 100 | 95 |

TABLE A-continued
Pre-emergence test/greenhouse
| Active compound of Preparation Example No. | Application rate (g of a.i./ha) | Echinochloa | Setaria | Amaranthus | Matricaria | Veronica |
|---|---|---|---|---|---|---|
| 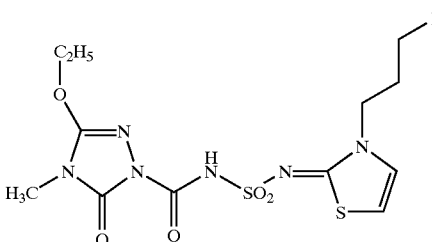 (1) | 60 | 100 | 100 | 100 | 100 | 100 |
| Active compound of Preparation Example No. | Application rate (g of a.i./ha) | Echinochloa | Amaranthus | Chenopodium | Matricaria | Veronica |
|---|---|---|---|---|---|---|
| 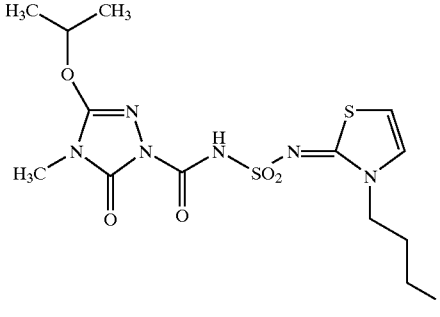 (125) | 125 | 90 | 70 | 95 | 100 | 100 |
| 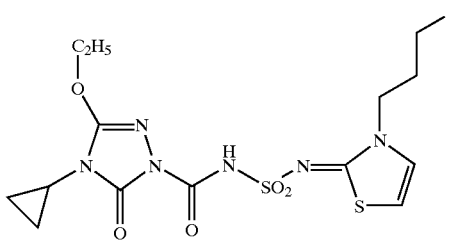 (130) | 125 | 100 | 100 | 100 | 100 | 100 |
| 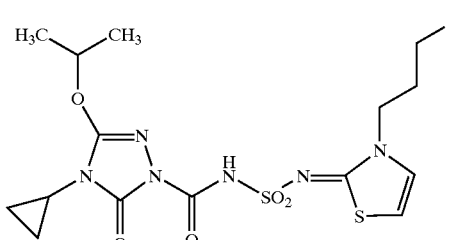 (131) | 125 | 80 | 100 | 95 | 100 | 95 |

TABLE A-continued

Pre-emergence test/greenhouse

| Active compound of Preparation Example No. | Application rate (g of a.i./ha) | Setaria | Amaranthus | Chenopodium | Matricaria | Veronica |
|---|---|---|---|---|---|---|
| (56) [structure] | 250 | 100 | 100 | 100 | 100 | 100 |

| Active compound of Preparation Example No. | Application rate (g of a.i./ha) | Amaranthus | Chenopodium | Matricaria | Veronica |
|---|---|---|---|---|---|
| (51) [structure] | 125 | 100 | 95 | 100 | 100 |

Example B
Post-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100 %=total destruction

In this test, for example, the compounds of Preparation Examples 1, 2, 9, 33, 34, 41, 48, 49, 55, 125, 130 and 131 exhibit very strong activity against weeds.

TABLE B

Post-emergence test/greenhouse

| Active compound of Preparation Example No. | Application rate (g of a.i./ha) | Setaria | Abu-tilon | Amaranthus | Chenopodium | Solanum | Stellaria |
|---|---|---|---|---|---|---|---|
| (2) [structure] | 60 | 90 | 90 | 90 | — | 95 | 90 |

TABLE B-continued

Post-emergence test/greenhouse

| Compound | | | | | | | |
|---|---|---|---|---|---|---|---|
| (9) | 60 | — | 90 | 90 | 80 | — | 90 |
| (33) | 125 | 80 | 100 | 100 | 100 | 95 | 95 |
| (34) | 125 | 70 | 95 | 100 | 100 | 100 | 100 |
| (41) | 125 | 70 | 90 | 90 | — | 90 | 95 |
| (48) | 125 | — | 80 | 95 | 100 | 80 | 80 |

TABLE B-continued

Post-emergence test/greenhouse

| Active compound of Preparation Example No. | Application rate (g of a.i./ha) | Echinochloa | Sorghum | Amaranthus | Polygonum | Veronica |
|---|---|---|---|---|---|---|
| (49) | 125 | — | 70 | 100 | 100 | 95 | 95 |
| (55) | 125 | — | 95 | 100 | 100 | 90 | 100 |
| (1) | 60 | 95 | 95 | 95 | 90 | 90 |

| Active compound of Preparation Example No. | Application rate (g of a.i./ha) | Abutilon | Polygonum | Solanum | Stellaria |
|---|---|---|---|---|---|
| (125) | 60 | 90 | 90 | 90 | 90 |

TABLE B-continued

Post-emergence test/greenhouse

| Active compound of Preparation Example No. | Application rate (g of a.i./ha) | Abutilon | Amaranthus | Chenopodium | Matricaria | Stellaria | Veronica |
|---|---|---|---|---|---|---|---|
| 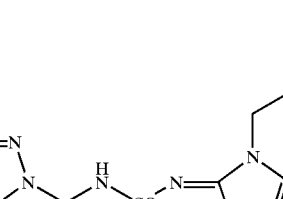 (130) | 60 | 95 | 100 | 100 | 100 | 95 | 100 |
| 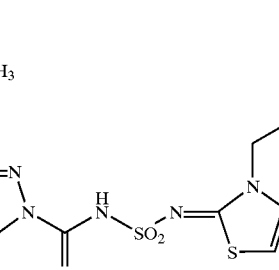 (131) | 60 | 90 | 100 | 95 | 95 | 95 | 90 |

What is claimed is:

1. A substituted thiazol(in)ylideneaminosulphonylamino(thio)-carbonyltriazolin-one of the formula (I),

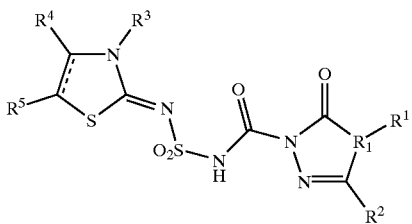

wherein

Q represents oxygen or sulphur;

$R^1$ is a moiety selected from the group consisting of hydrogen; amino; alkylideneamino; and an unsubstituted or substituted radical selected from the group consisting of alkyl, alkoxy, alkylamino, dialkylamino, alkanoylamino, alkenyl, alkinyl, alkenyloxy, cycloalkyl, cycloalkylalkyl, cycloalkylamino, aryl and arylalkyl;

$R^2$ is moiety selected from the group consisting of hydrogen; cyano; halogen; and an unsubstituted or substituted radical selected from the group consisting of alkyl, alkoxy, alkylthio, alkylsulphinyl, alkylsulphonyl, alkylamino, dialkylamino, alkenyl, alkinyl, alkenyloxy, alkenylthio, alkenylamino, cycloalkyl, cycloalkylalkyl, cycloalkyloxy, cycloalkylthio, cycloalkylamino, aryl, aryloxy, arylthio, arylamino, arylalkyl, arylalkoxy, arylalkylthio and arylalkylamino;

$R^3$ is an unsubstituted or substituted radical selected from the group consisting of alkyl, alkoxy, alkenyl, alkinyl, cycloalkyl, cycloalkylalkyl, aryl and arylalkyl;

$R^4$ represents hydrogen, cyano, halogen, unsubstituted alkyl or substituted alkyl;

$R^5$ represents hydrogen, cyano, halogen, unsubstituted alkly or substituted alkyl;

or salts of compounds of formula (I).

2. The compound of claim 1, wherein

Q represents oxygen or sulphur;

$R^1$ is a moiety selected from the group consisting of hydrogen; amino; $C_1$–$C_6$-alkylideneamino; a radical selected from the group consisting of $C_{1-C_6}$-alkyl, $C_2$–$C_6$-alkenyl, $C_2$–$C_6$-alkinyl, $C_1$–$C_6$-alkyloxy, $C_2$–$C_6$-alkenyloxy, $C_1$–$C_6$-alkylamino, di-($C_1$–$C_4$-alkyl)-amino, $C_1$–$C_4$-alkanoylamino, $C_3$–$C_6$-cycloalkyl, $C_3$–$C_6$-cycloalkyl-$C_1$–$C_4$-alkyl, phenyl and phenyl-$C_1$–$C_4$-alkyl;

fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl; fluorine-, chlorine- and/or bromine-substituted $C_2$–$C_6$-alkenyl or $C_2$–$C_6$-alkinyl; fluorine- and/or chlorine-substituted $C_1$–$C_6$-alkylamino, di-($C_1$–$C_4$-alkyl)-amino or $C_1$–$C_4$-alkanoyl-amino; fluorine-, chlorine-, bromine- and/or $C_1$–$C_4$-alkyl-substituted $C_3$–$C_6$-cycloalkyl or $C_3$–$C_6$-cycloalkyl-$C_1$–$C_4$-alkyl; and fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl or phenyl-$C_1$–$C_4$-alkyl;

$R^2$ is a moiety selected from the group consisting of hydrogen; cyano; fluorine; chlorine; bromine; iodine; a radical selected from the group consisting of alkyl, alkoxy, alkylthio, alkylsulphinyl, alkylsulphonyl, alkylamino or dialkylamino having in each case 1 to 6 carbon atoms in the alkyl group; a radical selected from the group consisting of alkenyl, alkenyloxy, alkenylthio or alkenylamino having in each case 2 to 6 carbon atoms in the alkenyl group; alkinyl having 2 to 6 carbon atoms; a radical selected from the group consisting of cycloalkyl, cycloalkylalkyl, cycloalkyloxy, cycloalkylthio or cycloalkylamino having in each case 3 to 6 carbon atoms in the cycloalkyl groups and, when present, 1 to 3 carbon atoms in the alkyl moiety; a radical selected from the group consisting of phenyl, phenoxy, phenylthio, phenylamino, benzyl, benzyloxy, benzylthio or benzylamino; fluorine-, chlorine-, bromine-, cyano-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl- or $C_3$-$C_6$-cycloalkyl-substituted alkyl, alkoxy, alkylthio, alkylsulphinyl, alkylsulphonyl, alkylamino or dialkylamino having in each case 1 to 6 carbon atoms in the alkyl group; fluorine-, chlorine- and/or bromine-substituted alkenyl, alkenyloxy, alkenylthio or alkenylamino having in each case 2 to 6 carbon atoms in the alkenyl groups; fluorine-, chlorine-, bromine-, cyano- and/or $C_1$–$C_4$-alkyl-substituted cycloalkyl, cycloalkylalkyl, cycloalkyloxy, cycloalkylthio or cycloalkylamino having in each case 3 to 6 carbon atoms in the cycloalkyl groups and, when present, 1 to 3 carbon atoms in the alkyl moiety; and fluorine-, chlorine-, bromine-, cyano-, nitro-, $C_1$–$C_4$-alkyl-, trifluoromethyl-, $C_1$–$C_4$-alkoxy, difluoromethoxy- or trifluoromethoxy-substituted phenyl, phenoxy, phenylthio, phenylamino, benzyl, benzyloxy, benzylthio or benzylamino;

$R^3$ represents a moiety selected from the group consisting of alkyl having 1 to 6 carbon atoms; alkoxy having 1 to 6 carbon atoms; alkenyl or alkinyl having in each case 2 to 6 carbon atoms; cycloalkyl or cycloalkylalkyl having in each case 3 to 6 carbon atoms in the cycloalkyl groups and, when present, 1 to 3 carbon atoms in the alkyl moiety; phenyl or benzyl; cyano-, carboxyl-, carbamoyl-, fluorine-, chlorine-, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted alkyl having 1 to 6 carbon atoms; cyano-, fluorine-, chlorine- or $C_1$–$C_4$-alkoxy-substituted alkoxy having 1 to 6 carbon atoms; cyano-, carboxyl-, carbamoyl-, fluorine-, chlorine-, bromine-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted alkenyl or alkinyl having in each case 2 to 6 carbon atoms; cyano-, carboxyl-, carbamoyl-, fluorine-, chlorine-, bromine-, $C_1$–$C_4$-alkyl-, $C_1$–$C_4$-alkyl-carbonyl-, $C_1$–$C_4$-alkoxy-carbonyl-, $C_1$–$C_4$-alkylamino-carbonyl- or di-$C_1$–$C_4$-alkyl-amino-carbonyl-substituted cycloalkyl or cycloalkylalkyl having in each case 3 to 6 carbon atoms in the cycloalkyl groups and, when present, 1 to 3 carbon atoms in the alkyl moiety; and, phenyl or benzyl, each of which is substituted by group selected consisting of:

nitro; cyano; carboxyl; carbamoyl; fluorine; chlorine; bromine; $C_1$–$C_4$-alkyl; $C_1$–$C_4$-alkoxy; $C_1$–$C_4$-alkylthio; $C_1$–$C_4$-alkylsulphinyl; $C_1$–$C_4$-alkylsulphonyl; and, fluorine-and/or chlorine-substituted substituted $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl;

$R^4$ represents hydrogen, cyano, fluorine, chlorine, bromine, an alkyl group having 1 to 4 carbon atoms or a fluorine or chlorine-substituted alkyl having 1 to 4 carbon atoms; and $R^5$ represents hydrogen, cyano, fluorine, chlorine, bromine, an alkyl group having 1 to 4 carbon atoms or a fluorine- and/or chlorine-substituted alkyl having 1 to 4 carbon atoms;

and the sodium, potassium, magnesium, calcium, ammonium, $C_1$-$C_4$-alkyl-ammonium, di-($C_1$-$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$– or $C_6$-cycloalkyl-ammonium or di-($C_1$–$C_2$-alkyl)-benzyl-ammonium salts of compounds of formula (I).

3. The compound of claim 1, wherein

Q represents oxygen or sulphur;

$R^1$ represents a moiety selected from the group consisting of unsubstituted or fluorine-, chlorine-, cyano-, methoxy- or ethoxy-substituted methyl, ethyl, n- or i-propyl; unsubstituted or fluorine-, chlorine- or bromine-substituted ethenyl, propenyl, butenyl, propinyl or butinyl; methoxy, ethoxy, n- or i-propoxy; allyloxy; methylamino, ethylamino, n- or i-propylamino, dimethylamino or diethylamino; and, unsubstituted or fluorine-, chlorine-, bromine-, methyl- or ethyl-substituted cyclopropyl;

$R^2$ represents a moiety selected from the group consisting of chlorine or bromine; unsubstituted or fluorine-, chlorine-, bromine-, cyano-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, n-, i-, s- or t-butylsulphinyl, n-, i-, s- or t-butylsulphonyl, methylamino, ethylamino, n- or i-propylamino, n-, i-, s- or t-butylamino, dimethylamino or diethylamino; unsubstituted or fluorine-, chlorine- and/or bromine-substituted ethenyl, propenyl, butenyl, ethenyloxy, propenyloxy, butenyloxy, propenylthio, butenylthio, propenylamino or butenylamino; propinyl, butinyl, propinyloxy, butinyloxy, propinylthio or butinylthio; unsubstituted or fluorine-, chlorine-, bromine-, cyano- and/or methyl-substituted cyclopropyl, cyclobutyl, cyclopentyl, cyclohexyl, cyclohexenyl, cyclopropyloxy, cyclobutyloxy, cyclopentyloxy, cyclohexyloxy, cyclopropylthio, cyclobutylthio, cyclopentylthio or cyclohexylthio; unsubstituted or fluorine-, chlorine-, bromine-, cyano-, methyl-, trifluoromethyl-, methoxy-, difluoromethoxy- or trifluoromethoxy-substituted phenyl, phenoxy, phenylthio, phenylamino, benzyl, benzyloxy, benzylthio or benzylamino;

$R^3$ is a moiety selected from the group consisting of unsubstituted or cyano-, carboxyl-, carbamoyl-, fluorine-, chlorine-, methoxy-, ethoxy-, n- or i-propoxy-, methylthio-, ethylthio-, n- or i-propyl-thio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethyl-amino-carbonyl-substituted methyl, ethyl, n- or i-propyl, n-, i-, s- or t-butyl; unsubstituted or cyano-, fluorine-, chlorine-, methoxy- or ethoxy-substituted methoxy, ethoxy, n- or i-propoxy; unsubstituted or cyano-, carboxyl-, carbamoyl-, fluorine-, chlorine-, bromine-, acetyl-, propionyl-, methoxycarbonyl-, ethoxycarbonyl-, n- or i-propoxycarbonyl-, methylaminocarbonyl-, ethylaminocarbonyl-, n- or i-propylamino-carbonyl-, dimethylaminocarbonyl- or diethyl-amino-carbonyl-substituted ethenyl, propenyl, butenyl, ethenyl, propinyl or butinyl; unsubstituted or cyano-, carboxyl-, carbamoyl-, fluorine-, chlorine-, bromine-, methyl-, ethyl-, n- or i-propyl-, n-, i-, s- or t-butyl-, acetyl-, propionyl-, methoxycarbonyl-, ethoxycarbonyl-, n- or i-propoxycarbonyl-, methylaminocarbonyl-, ethylamino-carbonyl-, n- or i-propylaminocarbonyl-, dimethylaminocarbonyl- or diethyl-amino-carbonyl-substituted cyclopropyl, cyclobutyl, cyclopentyl, cyclohexyl, cyclopropylmethyl, cyclobutylmethyl, cyclopentylmethyl or cyclohexylmethyl; unsubstituted phenyl or benzyl; and phenyl or benzyl each of which is substituted by nitro, cyano, carboxyl, carbamoyl, fluorine, chlorine, bromine, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, each of which may be unsubstituted or fluorine- and/or chlorine-substituted substituted;

$R^4$ represents hydrogen, cyano, fluorine, chlorine, bromine or unsubstituted or fluorine- and/or chlorine-substituted methyl, ethyl, n- or i-propyl; and $R^5$ represents hydrogen, cyano, fluorine, chlorine, bromine or unsubstituted or fluorine- and/or chlorine-substituted methyl, ethyl, n- or i-propyl.

4. A process for preparing the compound of claim 1, comprising:

(a) reacting a chlorosulphonylamino(thio) carbonyltriazolinone of the formula (ll)

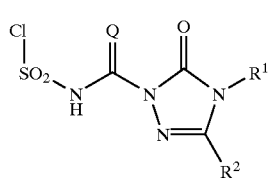
(II)

wherein
Q, $R^1$ and $R^2$ are each as defined in claim 1 with an iminothiazoli(di)ne of the formula (III) or an acid adduct thereof

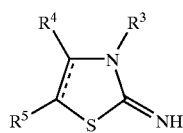
(III)

wherein $R^3$, $R^4$ and $R^5$ are each as defined in claim 1, if desired in the presence of a reaction auxiliary and/or a diluent, and if appropriate, converting the resulting compounds into salts, or (b) reacting a triazolinone of the formula (IV)

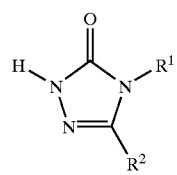
(IV)

wherein
$R^1$ and $R^2$ are each as defined above
with a chlorosulphonyl iso(thio)cyanate of the formula (V)

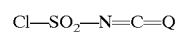
Cl—SO$_2$—N=C=Q    (V)

wherein
Q is as defined above
if desired in the presence of a reaction auxiliary and/or a diluent,
and reacting the resulting chlorosulphonylamino(thio) carbonyltriazolinones of the formula (II)

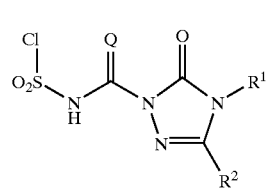
(II)

wherein
Q, $R^1$ and $R^2$ are each as defined above,
with an iminothiazoli(di)ne of the formula (III)

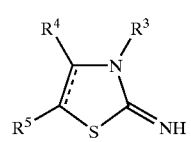
(III)

wherein
$R^3$, $R^4$ and $R^5$ are each as defined above,
if desired in the presence of a reaction auxiliary and/or a diluent,
and, if appropriate, the resulting compounds of the formula (I) are converted into salts.

5. A herbicidal composition, comprising one or more compounds of claim 1 and a member selected from the group consisting of extenders, surfactants and mixtures thereof.

6. A method for controlling weeds comprising allowing an effective amount of the compound of claim 1 allowed to act on the weeds or their habitat.

7. A process for preparing herbicidal compositions, comprising mixing the compound of claim 1 with extenders and/or surfactants.

* * * * *